(12) United States Patent
Bennett et al.

(10) Patent No.: US 8,006,633 B2
(45) Date of Patent: Aug. 30, 2011

(54) EMBROIDERED ELECTRODE

(75) Inventors: Genevieve Bennett, London (GB);
Philip A. H. Clarke, Leatherhead (GB);
Warren B. Valentine, Preston (GB)

(73) Assignee: Koninklijke Philips Electronics N.V., Eindhoven (NL)

( * ) Notice: Subject to any disclaimer, the term of this patent is extended or adjusted under 35 U.S.C. 154(b) by 264 days.

(21) Appl. No.: 10/558,489

(22) PCT Filed: May 21, 2004

(86) PCT No.: PCT/IB2004/001766
§ 371 (c)(1),
(2), (4) Date: Nov. 28, 2005

(87) PCT Pub. No.: WO2004/105863
PCT Pub. Date: Dec. 9, 2004

(65) Prior Publication Data
US 2007/0028821 A1 Feb. 8, 2007

(30) Foreign Application Priority Data
May 31, 2003 (GB) .................................. 0312517.6

(51) Int. Cl.
*H05B 3/34* (2006.01)

(52) U.S. Cl. .................. 112/475.22; 219/212; 219/217; 219/528; 219/529; 219/543; 219/544; 219/545; 219/548; 219/549; 338/47; 338/22 R

(58) Field of Classification Search ............. 112/475.22; 219/217, 545, 548, 549, 212, 528, 529, 543, 219/544; 338/47, 22 R, 99; 600/383, 391, 600/384, 396, 397, 547; 607/152, 48
See application file for complete search history.

(56) References Cited

U.S. PATENT DOCUMENTS

| | | | |
|---|---|---|---|
| 4,417,581 A * | 11/1983 | Dawson ....................... 600/383 |
| 4,441,500 A | 4/1984 | Sessions et al. |
| 4,654,511 A * | 3/1987 | Horsma et al. ................ 219/548 |
| 4,729,377 A | 3/1988 | Granek et al. |
| 4,867,166 A * | 9/1989 | Axelgaard et al. ............ 600/391 |
| 4,983,814 A * | 1/1991 | Ohgushi et al. ............... 219/545 |
| 5,111,025 A * | 5/1992 | Barma et al. .................. 219/217 |
| 5,263,481 A | 11/1993 | Axelgaard |
| 6,047,203 A | 4/2000 | Sackner et al. |
| 6,229,123 B1 * | 5/2001 | Kochman et al. ............. 219/549 |
| 7,145,432 B2 * | 12/2006 | Lussey et al. ................... 338/47 |
| 2001/0002669 A1 * | 6/2001 | Kochman et al. ............. 219/545 |
| 2004/0252007 A1 * | 12/2004 | Lussey et al. ................... 338/47 |

FOREIGN PATENT DOCUMENTS

| | | |
|---|---|---|
| JP | 2001295149 | 10/2001 |
| WO | WO0102052 A2 | 1/2001 |
| WO | WO01/02052 * | 11/2001 |
| WO | WO01/88935 * | 11/2001 |
| WO | WO 01/88935 A1 * | 11/2001 |
| WO | WO0230279 A1 | 4/2002 |

OTHER PUBLICATIONS

Kadolph, S. & Langford, A. (1998) Textiles. Upper Saddle River, NJ: Merrill, pp. 285-299.*
ISR of International Application No. PCT/IB2004/001766 Contained in International Publication No. WO2004/105863.
Written Opinion of the International Searching Authority for International Application No. PCT/IB2004/001766.

* cited by examiner

*Primary Examiner* — Leszek Kiliman

(57) ABSTRACT

An embroidered electrode (10) consists of embroidered elements (12, 13, 14) of electrically conductive thread sewn on a backing material (11). Within a given element the orientation of stitching is selected to be parallel to the direction in which the element extends.

13 Claims, 2 Drawing Sheets

EMBROIDERED ELECTRODE

Figure 1:
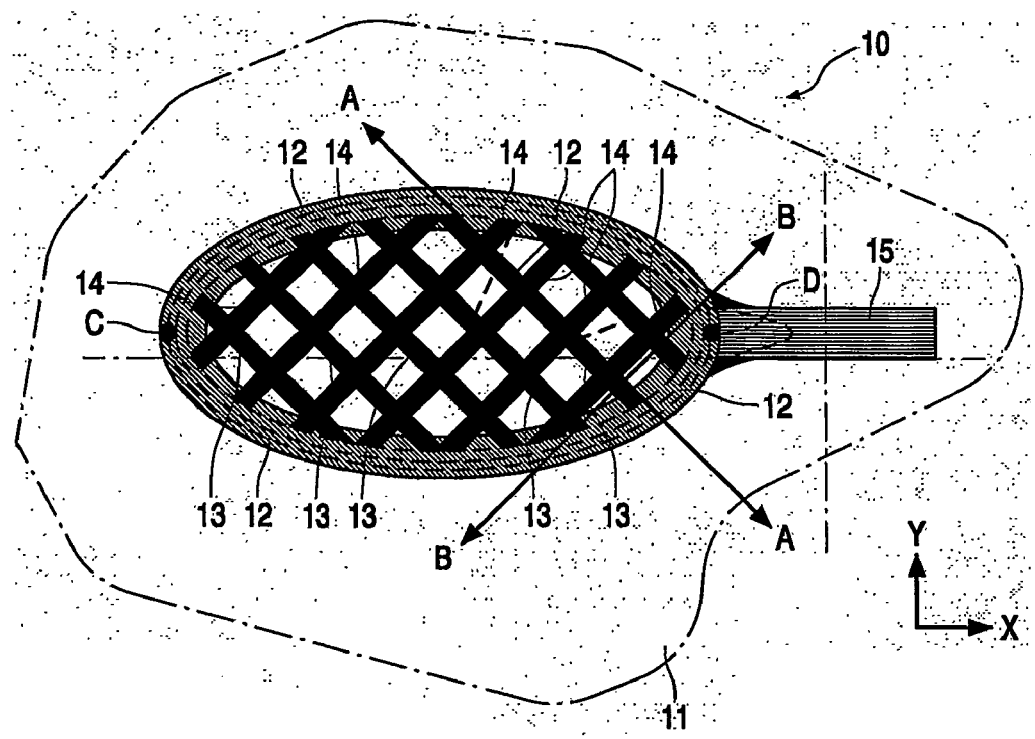

The present invention relates to fabric electrodes, in particular to fabric electrodes that are of an embroidered construction.

It is known to apply electrodes to a body for either detection of signals from the body, for example during electrocardiogram measurements, or for application of electrical signals to the body, for example during muscle, organ or nerve stimulation. Two requirements of an electrode are that it functions adequately to transfer electrical energy between the electrode and body and that it is comfortable to the wearer. Making the electrode soft to the touch and flexible can enhance comfort.

Comfort is especially important during ambulatory use or sports training use because it is usually desirable that the wearer is unaware of the presence of the electrode. In the case of ambulatory use the electrode may be worn for a long time and in the case of sports training it is important that an athlete is not distracted by the presence of the electrode.

In principle flexible fabric electrodes are capable of offering the comfort required in ambulatory and sports training applications (as well as other applications) if suitable materials and construction techniques are chosen. Furthermore it is possible to incorporate fabric electrodes into garments as described in WO-A-01/02052 which relates to a garment adapted to be used as a medical electrode, the garment comprising at least two different zones with at least one of the zones being an electro-conductive zone to be used as an electrode, the electro-conductive zone comprising metal fibres; at least one other of said zones being an elastic zone, being a textile fabric of electrically non-conductive yarns. The electro-conductive zone may be knitted and the construction is described in some detail. WO-A-01/02052 also makes brief mention of the fact that the garment can comprise an elastic zone on which an electro-conductive zone is embroidered using electrically conductive yarns, although little further information is given.

The applicants have experimented with knitted fabric electrodes that are suitable for performing electrocardiograph (ECG) measurements of a human under ambulatory conditions. It is recognised that by using electrodes that are mechanically flexible they conform to a user to provide added comfort and better contact to the skin. Furthermore, if the electrodes are incorporated into a garment and can flex in conformity with the garment, this can also contribute to user comfort. However, results of the experiments have also shown that under ambulatory or sports training conditions the use of an electrode that is mechanically flexible can suffer because the flexing and/or partial stretching of the electrode during use has the undesirable effect of generating movement-induced electrical noise on the detected ECG measurements obtained using the electrode. Although the detected signal can be processed to improve the actual ECG signal, in some cases the movement induced noise could completely mask the small electrical ECG signal that is detectable from the surface of the skin. The overall effect of the movement induced noise may be minimised by increasing the content of electrically conductive material in the electrode-to-skin contact region but this is not always possible or desirable due to manufacturing limitations or the detrimental effect on user comfort.

It is an object of the present invention to provide an improved electrode having an embroidered element.

In accordance with a first aspect of the present invention there is provided an electrode including an embroidered element comprising electrically conductive thread embroidered onto a backing characterised in that the element comprises at least one portion in which the thread is stitched with an orientation selected to optimise performance of the electrode.

Advantageously, local variations in stitch orientation can be used to govern the effective electrical resistance of that electrical element when considered as part of an embroidered pattern.

Optionally, the orientation of the stitching is selected such that thread direction is substantially parallel with the required direction of electrical conduction. Advantageously this should lead to improved electrical conductivity of the element in the direction of electrical conduction.

In accordance with a second aspect of the present invention there is provided an embroidered electrode comprised of electrically conductive thread stitched on a backing material to form one or more embroidered element wherein said electrode comprises a primary embroidered element and one or more further embroidered element extending from a portion of the primary element.

Optionally, the primary embroidered element is arranged to loop back on itself.

Optionally, the at least one further embroidered element extends towards a portion of the primary element.

A portion of one or more of the embroidered elements may be produced from the electrically conductive thread that is stitched with an orientation selected to optimise performance of the electrode. Preferably the orientation of the stitching is selected such that thread direction is substantially parallel with the required direction of electrical conduction in the locality of the portion.

In one possible arrangement, the primary embroidered element forms a peripheral electrode component and at least one of the further embroidered elements extends within the periphery described by the peripheral component from one portion of the primary element to another portion of the primary element. In this case at least one of the further embroidered elements may intersect and cross over another one of the further embroidered elements.

The electrically conductive thread may be silverised polyamide.

In accordance with a third aspect of the present invention there is provided a garment or accessory comprising an embroidered electrode of the first or second aspect.

In accordance with a fourth aspect of the present invention there is provided a device comprising an embroidered electrode of the first or second aspect.

Figure 2A:
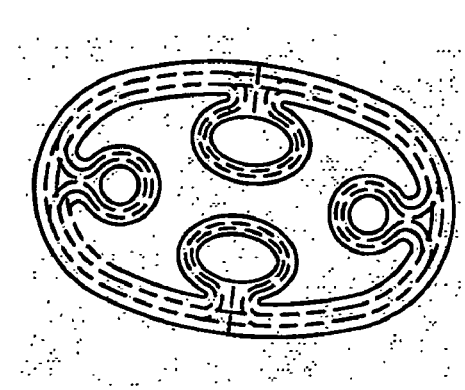
Figure 2B:
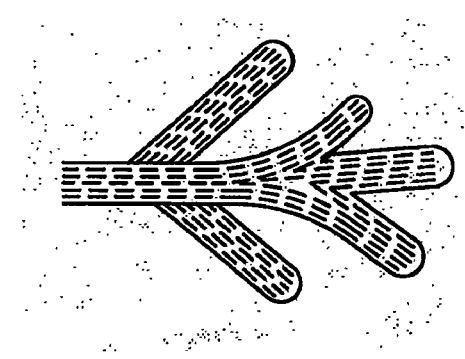
Figure 2C:
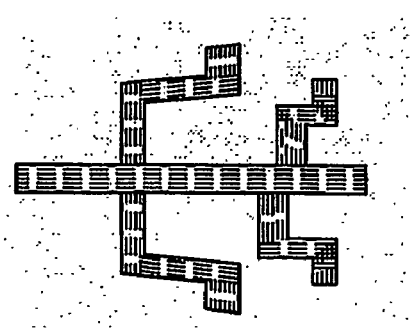

These an other aspects of the present invention will now be described with reference to the Figures of the accompanying drawings in which:

FIG. 1 shows a front view of a first embodiment of an embroidered electrode of the present invention; and FIGS. 2a to 2c show alternative embroidering patterns of further embodiments of embroidered electrodes of the present invention.

It should be noted that the drawings are diagrammatic and not drawn to scale. Relative dimensions and proportions of parts of the Figures have been shown exaggerated or reduced in size for the sake of clarity and convenience in the drawings. The same reference signs are generally used to refer to corresponding or similar features in the different embodiments.

An embroidered electrode 10 is formed by an embroidering process in which electrically conductive thread is attached onto a backing material 11 by stitching the thread in a pattern. At least the exterior surface of the thread should be electrically conductive. The backing material is non-conductive felt sheet. In the case of the embroidered electrode 10 the embroidered pattern consists of a first embroidered element 12 that is generally oval in shape and continuous to form a peripheral component of the electrode 10. The embroidered pattern also consists of further embroidered elements in the form of a first plurality of substantially linear elements 13 that run parallel to each other and are spaced apart from each other to extend within the peripheral component from a portion of the first element 12 to another portion of it. In the arrangement shown, each linear element 13 of the first plurality extends from and to a different part of the peripheral component formed by first element 12. The embroidered pattern also consists of further embroidered elements in the form of a second plurality of substantially linear elements 14 that run parallel to each other and are spaced apart from each other to extend within the peripheral component from a portion of the first element 12 to another portion of it. In the arrangement shown, each linear element 14 of the second plurality extends from and to a different part of the peripheral component formed by first element 12. The first plurality of substantially linear elements 13 extend in a direction that is substantially 90 degrees to the direction that the second plurality of substantially linear elements 14 extend. When the electrode is arranged to be viewed such that the major axis of the oval described by the first embroidered element 12 is horizontal and deemed to extend in a direction of zero degrees, the first plurality of substantially linear elements 13 extend in a direction of +45 degrees to the major axis and the second plurality of substantially linear elements 14 extend in a direction of +135 degrees to the major axis.

The applicants have recognised that the process of embroidering permits the stitch direction (orientation) to be chosen at will in the locality of the stitching. Therefore unlike a knitting or weaving process which places a restriction on the direction of woven or knitted yarn, the embroidery process permits stitch direction to be selected at a particular locality of an embroidered pattern independently of the stitch direction selected at any other locality of the embroidered pattern. The applicants have also recognised that when embroidering by stitching with an electrically conductive thread good electrical conductivity is provided along the thread and so therefore good electrical conductivity in a particular locality of an embroidered pattern will be obtained in the direction of the stitch orientation. Therefore, for a given embroidered pattern the careful choice of stitch direction in various localities of the pattern can be used to control the electrical conductivity of the embroidered pattern. In the case of an embroidered pattern forming an electrode the stitch direction will normally be selected in various localities of the pattern to optimise electrical conductivity of the pattern overall.

The applicants have also recognised that when an attempt is made to stretch a portion of an embroidered pattern in a direction parallel to (i.e. along) the portions' stitch direction the change in electrical conductivity is low in comparison to when the portion is stretched in a direction that is not parallel to the portions stitch direction. This is thought to be because the main mechanism of electrical conduction along stitch direction is via the electrically conductive thread whereas the main mechanism of conduction in a direction orthogonal to the stitch direction will rely on inter-thread contact, the effectiveness of such contact being susceptible to stretching and flexing of the embroidered portion because contact between adjacent conductive threads is being disturbed. If the change in electrical conductivity is low when stretched or flexed then the associated movement induced electrical noise observed when measuring biometric signals using an electrode having an embroidered pattern of electrically conductive material is also advantageously low. The embroidered electrode is generally resistant to stretch by nature of it being embroidered although during use it is possible for small amounts of stretch to occur.

The stitch direction of the first plurality of substantially linear elements 13 is parallel to the direction in which those linear elements 13 extend. Therefore, if an attempt is made to stretch the sensor in a direction that is parallel to the direction of the first plurality of substantially linear elements 13, denoted by line A-A, the change in electrical resistance along the length of a linear element will be small, typically in the order of less than one tenth of an ohm. The stitch direction of the second plurality of substantially linear elements 14 is parallel to the direction in which those elements extend. Therefore, if an attempt is made to stretch the sensor in a direction that is parallel to the direction of the second plurality of substantially linear elements 14, denoted by line B-B, the change in electrical resistance along the length of a linear element will be small, typically in the order of less than one tenth of an ohm.

When the electrode is stretched in a direction different to A-A or B-B where will still be adequate conduction along conductive stitched yarn that makes up the electrode pattern which helps to minimise the change of electrical properties, hence limit electrically induced noise.

Optionally further embroidered elements may be added to the embroidered pattern to run in a direction different to the first plurality 13 and second plurality 14 of elements.

For example, with reference to FIG. 1 a further plurality of elements could run in a direction (denoted X) parallel to the major axis of the oval described by the peripheral component 10 and/or further plurality of elements could run in a direction (denoted Y) which is parallel to the minor axis described by the peripheral component 10.

The process of embroidering is well known to the person skilled in the art, the process consisting of stitching thread to a backing material 11 to build up an embroidered pattern. Two threads are used in the stitching process—one thread being predominantly situated on a first surface of an embroidered backing material and another thread being predominantly situated on a second (opposite) surface of the backing material, one thread being interlooped with the other thread by virtue of the stitching process. In the case of the first embodiment electrode 10, the upper surface shown by the plan view of FIG. 1 is the surface of the electrode which is worn against the skin during use. Therefore the pattern shown is formed on the upper surface by using electrically conductive thread. Optionally, the thread stitched on the other surface (not visible) may be conductive or non-conductive: use of conductive thread has the potential to increase electrical conductivity overall but use of a non-conductive thread will assist where it is necessary to electrically insulate the electrode on its backside.

In the case of the first embodiment electrode 10 the electrically conductive thread is silverised polyamide, although other suitable electrically conductive threads could be used instead or in addition as will be appreciated by the person skilled in the art, such as a thread of polyester and stainless steel. Factors which govern the choice of thread include electrical and physical characteristics of the thread, which are dictated by manufacturing considerations, required comfort of the finished electrode during use and whether or not the electrode is to be washable.

A straightforward DC resistance measurement performed on the first embodiment electrode 10 comprising embroidered silverised polyamide thread showed that the resistance measured across one end of the first embroidered element 12 to the other, that is in the direction of the major axis of the oval, using measuring points denoted 'C' and 'D' in FIG. 1, was in the region of one ohm, specifically 0.7 ohms. Stretching or otherwise distorting the electrode gave very little change in electrical resistance measured and the same measurement under stretch gave a reading of 0.6 ohms.

Where the first plurality of linear elements 13 intersect and cross over the second plurality of linear elements, they are in physical and therefore electrical contact with each other by virtue of the stitching process of embroidering. Each of the first and second plurality of linear elements 13, 14 intersect with the first embroidered element 12 that forms the periphery of the electrode: all linear elements are in physical and therefore electrical contact with the first embroidered element 12 by virtue of the stitching process.

The electrode 10 is provided with a contact terminal 15 which also includes electrically conductive thread, the contact terminal being stitched to extend to and establish physical and electrical contact with the first embroidered element 12. The contact terminal 15 is used to electrically connect the electrode to electrical or electronic equipment.

The stitch orientation of stitches making up the first embroidered element 12 is preferably varied around the generally oval shape so that at a given part of the element 12 the stitches are always in line with the path taken by the element 12.

During use of the electrode for detecting signals, electrical signals detected from a persons skin make their way from the point of detection of the signal on the electrode through the embroidered pattern by the route of lowest electrical resistance to electrode contact terminal 15. This route may be via the first embroidered element 12 and/or the first 13 and second 14 plurality of electrically conductive elements. Indeed, the signals may zigzag their way via the crossing points of first 13 and second 14 electrically conductive elements to contact terminal 15, By including at least one further element running in the direction (denoted X) parallel to the major axis of the oval described by peripheral component 10, say from points denoted in FIG. 1 by C and D, performance of the electrode in transferring electrical current to or from the body may be improved.

The shortest route of least electrical resistance from any point of the embroidered pattern to terminal 15 will generally be the shortest route through the pattern, although as already explained the orientation of the embroidered stitches in any locality of the embroidered pattern can be chosen to govern the path of least electrical resistance from one portion of the embroidered pattern to another, depending on the intended application of the electrode. Indeed, this approach of locally changing stitch orientation can be used to advantage if the intended use of the electrode is to deliver current to the body, the stitch orientation being chosen so that the electrode can distribute current from the electrode to body more evenly over the area of the electrode than would otherwise be the case, and avoid so called 'hot spots'.

While the first embroidered element 12 is shown to be oval it may assume other shapes, for example circular, square, rectangular or in the form of some other polygon.

Other embodiments of the electrode are possible without departing from the present invention, a selection of which are shown in FIGS. 2a to 2c. In all cases, at least a portion of the embroidered pattern consists of stitching that is stitched in a direction substantially parallel, i.e. in line, with the path taken by the embroidered pattern in the locality of a given stitch. The direction of the shading or dashes in FIGS. 2a, b, c is intended to indicate stitch direction.

From reading the present disclosure other modifications will be apparent to persons skilled in the art. Such modifications may include other features which are already known in the design, manufacture and use of electrodes, garments or accessories provided with such electrodes, textiles and embroidery and associated manufacture and construction techniques and applications thereof and which may be used instead of or in addition to features already described herein.

The invention claimed is:

1. An electrode including an embroidered element comprising electrically conductive thread embroidered onto a backing characterised in that the element comprises a first portion in which the thread is stitched with an orientation such that thread direction is substantially parallel with a first direction of electrical conduction and a second portion in which the thread is stitched with an orientation such that thread direction is substantially parallel with a second direction of electrical conduction, the first and second portions contacting in at least one location.

2. An embroidered electrode comprised of electrically conductive thread stitched on a backing material to form one or more embroidered element wherein said electrode comprises a primary embroidered element and one or more further embroidered element extending from a portion of the primary element, wherein the primary embroidered element forms a peripheral electrode component and at least one of the further embroidered elements extends within the periphery described by the peripheral component from one portion of the primary element to another portion of the primary element.

3. An embroidered electrode in accordance with claim 2 wherein the primary embroidered element is arranged to loop back on itself.

4. An embroidered electrode in accordance with claim 2 wherein the at least one further embroidered element extends towards a portion of the primary element.

5. An embroidered electrode in accordance with claim 2 wherein a portion of one or more of the embroidered elements is produced from the electrically conductive thread which is stitched with an orientation selected to optimise performance of the electrode.

6. An embroidered electrode in accordance with claim 2 wherein at least one of the further embroidered elements intersects and crosses over another one of the further embroidered elements.

7. An embroidered electrode of claim 5 wherein the orientation of the stitching is selected such that thread direction is substantially parallel with the required direction of electrical conduction in the locality of the portion.

8. An embroidered electrode in accordance with claim 1 wherein the electrically conductive thread is silverised polyamide.

9. A garment or accessory comprising an embroidered electrode in accordance with claim 1.

10. A device comprising an embroidered electrode in accordance with claim 1.

11. An embroidered electrode in accordance with claim 2 wherein the electrically conductive thread is silverised polyamide.

12. A garment or accessory comprising an embroidered electrode in accordance with claim 2.

13. A device comprising an embroidered electrode in accordance with claim 2.

* * * * *